United States Patent [19]

Vennerstrom

[11] Patent Number: 5,510,356
[45] Date of Patent: Apr. 23, 1996

[54] BISQUINOLINES AND PROCESSES FOR THEIR PRODUCTION AND USE TO TREAT MALARIA

[75] Inventor: Jonathan L. Vennerstrom, Omaha, Nebr.

[73] Assignee: University of Nebraska Board of Regents, Lincoln, Nebr.

[21] Appl. No.: 770,638

[22] Filed: Oct. 3, 1991

[51] Int. Cl.$^6$ .......................... A61K 31/47; C07D 215/38
[52] U.S. Cl. .......................... 514/313; 514/895; 546/159
[58] Field of Search ................ 546/159; 514/313, 514/895

[56] References Cited

U.S. PATENT DOCUMENTS

| | | | |
|---|---|---|---|
| 2,050,971 | 8/1936 | Jensch | 546/159 |
| 2,791,582 | 5/1957 | Austin et al. | 546/159 |
| 3,027,378 | 3/1962 | Stark | 546/159 |
| 3,668,207 | 6/1972 | Carney | 546/159 |
| 3,875,165 | 4/1975 | Archibald et al. | 514/895 X |
| 3,948,920 | 4/1976 | Nabih | 514/895 X |
| 3,953,453 | 4/1976 | Grethe et al. | 514/895 X |
| 3,971,789 | 7/1976 | Archibald | 514/895 X |
| 5,110,935 | 5/1992 | Pirson | 514/895 X |

*Primary Examiner*—Gary L. Geist
*Assistant Examiner*—Catherine Scalzo
*Attorney, Agent, or Firm*—Janet E. Reed; Dann, Dorfman, Herrell and Skillman

[57] ABSTRACT

The present invention relates to new bisquinolines useful in the treatment of malaria and to processes for the production thereof. The invention also relates to methods for the treatment of malaria and, in particular, to the treatment of chloroquine-resistant strains of malaria. The compounds of the invention have the following formula:

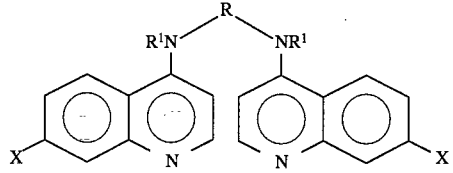

FORMULA I wherein R is a bivalent radical derived from an acyclic or cyclic hydrocarbon by removal of one hydrogen atom from each of two different carbon atoms. R' is hydrogen or lower alkyl (generally containing between about 1 and about 4 carbon atoms). X is hydrogen (—H), fluoro (—F), chloro (—Cl), bromo (—Br), trifluoromethyl (—CF$_3$), cyano (—CN), or methylsulfoxide (—SOCH$_3$). In its acyclic form, R generally contains at least two, and no more than about 12, carbon atoms and, preferably, is an unsubstituted straight or branched alkane. In its cyclic form, R contains at least three and, generally, no more than about eight carbon atoms and, preferably, is an unsubstituted cycloalkane. In a preferred embodiment, this invention relates to N,N-bis(7-chloroquinolin-4-yl)alkane diamines which are active against chloroquine-resistant malaria.

The bisquinolines of this invention are useful agents against chloroquine-resistant malaria. ±-Trans-N$^1$,N$^2$-Bis(7-chloroquinolin-4-yl)cyclohexane-1,2-diamine is highly preferred for treatment of chloroquine-resistant malaria. This compound is one of the most potent antimalarials discovered to date and is clearly unique in its in vivo activity –80% and 100% cure rates being achieved at doses of 160 and 320 mg/kg, respectively.

20 Claims, No Drawings

BISQUINOLINES AND PROCESSES FOR THEIR PRODUCTION AND USE TO TREAT MALARIA

FIELD OF THE INVENTION

The present invention relates to new bisquinolines useful in the treatment of malaria and to processes for the production thereof. The invention also relates to methods for the treatment of malaria and, in particular, to the treatment of chloroquine resistant strains of malaria. In a preferred embodiment, this invention relates to N,N-bis(7-chloroquinolin-4-yl)alkane diamines which are active against chloroquine-resistant malaria.

BACKGROUND OF THE INVENTION

In the following discussion, a number of citations from professional journals are included for the convenience of the reader. These citations are in abbreviated form in the text by author and year only. The full citation of each is set forth in the References section at the end of the specification. While these citations more fully describe the state of the art to which the present invention pertains, the inclusion of these citations is not intended to be an admission that any of the cited publications represent prior art with respect to the present invention.

By a large margin, malaria is the most prevalent disease in the world. It is estimated for the year 1986 that some 489 million people contracted malaria, 2.3 million of whom died from the disease (Sturchler, 1989). Whereas effective antimalarial drugs exist, drug-resistance, particularly resistance to chloroquine (CQ), the most useful antimalarial drug, has become an enormous problem (Payne, 1987).

Quinoline antimalarials such as quinine, mefloquine, and amodiaquine are active to various extents against CQ-resistant malaria (Geary and Jensen, 1983; Geary et al., 1987; Knowles et al., 1984; Watkins et al., 1984; Cowman and Foote, 1990; Sowunmi et al., 1990). Although Cowman and Foote (1990) suggest that CQ resistance may dispose the parasite to resistance to other quinolines, LeBras et al. (1983), Schmidt et al. (1977), Geary and Jensen (1983) and Oduola et. al. (1988) observe a significant lack of cross-resistance among quinoline-containing antimalarials.

It is an object of this invention to provide a new class of quinolines which are active against malaria and, in particular, CQ resistant malaria. The compounds of this invention are bisquinolines.

Many prior art bisquinolines have been reported to be inactive against malaria. These include the succinic acid diester of amodiaquine as a potential repository form (Elslager et al, 1969), and bisquinolines lacking either a 4-amino function or with a bridge at the 3 rather than the 4-position (Nasr et al, 1979; Nasr et al, 1978).

Examples of bisquinolines which have been reported to be active against malaria include several bisquinolylpiperazines such as piperaquine, hydroxypiperaquine, dichloroquinazine, 12494RP (Benazet, 1965; 1967; Lafaix et al., 1967; LeBras et al., 1983; Li et al., 1981a; 1981b; 1984; Zhang et al., 1987; Li and Huang, 1988; Chen et al, 1982), and 1,4-bis(7-chloro-4-quinolyl-amino)piperazine (Singh et al., 1971). In general, these bisquinolines are more potent than CQ, and are active against CQ-resistant malaria. Both piperaquine (PQ) and hydroxypiperaquine are claimed to be very effective against CQ-resistant malaria in China (Chen et al., 1982; Li et al., 1981b; 1984; Li and Huang, 1988).

Each of these drugs also has a longer duration of action, and less toxicity when compared to CQ (Li et al., 1981a; Lin et. al., 1982). Dichloroquinazine is active against CQ-resistant falciparum malaria (LeBras et al., 1983), and a mixture of 12,494RP and dichloroquinazine is clinically effective against falciparum malaria and exerts a suppressive effect lasting for 3 weeks (Lafaix et al. 1967; Benazet, 1965). Resistance to dichloroquinazine, however, is noted for a CQ-resistant strain of *P. berghei* (Warhurst, 1966). Although 1,4-bis(7-chloro-4-quinolylamino)piperazine has not been screened against CQ-resistant malaria, it is significantly more effective than is CQ against *P. berghei* in mice (Singh et al., 1971).

This invention relates to a new class of bis-4-aminoquinoline antimalarial agents. These agents exhibit potent activity against CQ-resistant malaria in the in vitro and in vivo tests hereinafter described.

SUMMARY OF THE INVENTION

In accordance with the present invention novel N,N-bis(7-substituted-quinolin-4-yl)alkane diamines are provided. In one embodiment, these compounds can be depicted by the following general formula:

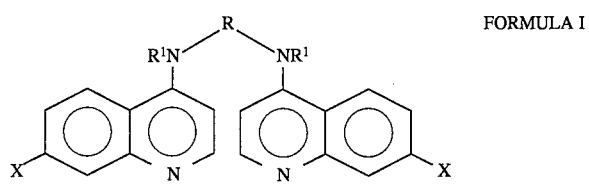

FORMULA I wherein R is a bivalent radical derived from an acyclic or cyclic hydrocarbon by removal of one hydrogen atom from each of two different carbon atoms. R' is hydrogen or lower alkyl (generally containing between about 1 and about 4 carbon atoms). X is hydrogen (—H), fluoro (—F), chloro (—Cl), bromo (—Br), trifluoromethyl (—$CF_3$), cyano (—CN), or methylsulfoxide (—$SOCH_3$). In its acyclic form, R generally contains at least two, and no more than about 12, carbon atoms and, preferably, is an unsubstituted straight or branched alkane. In its cyclic form, R contains at least three and, generally, no more than about eight carbon atoms and, preferably, is an unsubstituted cycloalkane.

It is believed that no compound within the scope of the above formula, i.e., N,N-bis(7-substituted-quinolin-4-yl)alkane diamines, has been described in the prior art, aside from $N^1$, $N^2$-bis(7-chloroquinolin-4-yl)ethane-1,2-diamine (Pearson et al., 1946). This compound has the following structural formula:

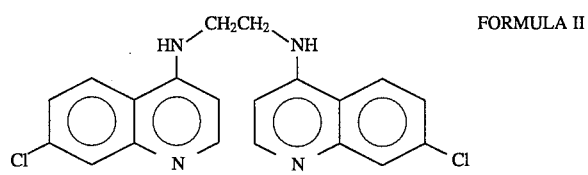

FORMULA II

The Pearson et al reference does not disclose this bisquinoline to have antimalarial properties. As is shown hereinafter, however, treatment of malaria parasites with this prior art compound, in accordance with the antimalarial methods of this invention, has resulted in antimalarial activity. As will be described more fully hereinafter, however, the next higher homologs of this compound, as well as other analogs thereof, exhibit unexpectedly higher antimalarial activity than the Pearson et al compound. Therefore, referring to Formula I above, an especially preferred embodiment of this invention is where R contains at least 3 carbon atoms.

Compounds of the following formula, wherein R is cyclic, constitute a preferred embodiment of this invention:

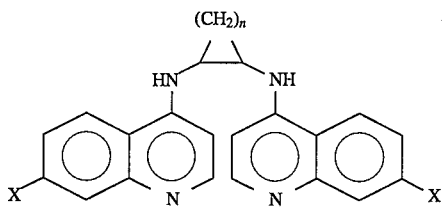

FORMULA III wherein X is as defined above and n is a whole integer from 1 through about 6, 4 being especially preferred because of the exceptional activity exhibited by ±-trans-$N^1,N^2$-Bis(7-chloroquinolin-4-yl)cyclohexane-1,2-diamine (Table I, compound 3).

The following formula, wherein R is acyclic, constitutes another embodiment of this invention:

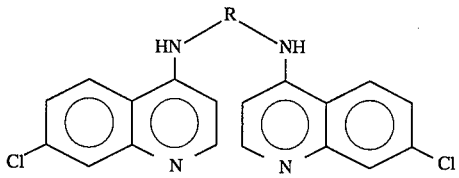

FORMULA IV wherein R is selected from the group consisting of $CH_2CH(CH_3)$, $(CH_2)_3$, $(CH_2)_4$, $(CH_2)_5$, $(CH_2)_3CH(CH_3)CH_2$, $(CH_2)_6$, $(CH_2)_7$, $(CH_2)_8$, $(CH_2)_9$, $(CH_2)_{10}$, $(CH_2)_{11}$, and $(CH_2)_{12}$, and other preferably lower-alkyl substituted derivatives thereof.

A method for the treatment of malaria constitutes another embodiment of this invention. This method comprises administering to a host an N,N-bis(7-substituted-quinolin-4yl)alkane diamine of this invention in a pharmaceutically acceptable dosage form containing an amount of said diamine which is effective in treating malaria. Ideally, the effective dose for treating malaria is that dose which is toxic to the malaria parasite infecting the host, but below the threshold of significant toxicity to the host. Generally, for the compounds of this invention this dose ranges from about 5 mg to about 100 mg per kilogram of host body weight. Because the compounds of this invention exhibit high therapeutic indices, it is possible, but generally not economically practical, to employ higher doses up to even 500 mg/kg and higher. Normally, because the compounds of this invention have such high antimalarial activity, doses of between about 5 and about 50 mg/kg host body weight are employed.

DETAILED DESCRIPTION OF THE INVENTION

Chemistry

The bisquinolines of this invention can be produced via a displacement reaction with 4,7-dichloroquinoline, alkanediamine, and triethylamine in a 2:1:2 ratio using N-methylpyrrolidinone as solvent. For the production of compounds 1–13 (see Table I) no success resulted with the method of Singh et al. (1971) where $K_2CO_3$ was used as base with ethoxyethanol as solvent. Substitution of triethylamine for $K_2CO_3$, however, gave good results. Furthermore, substitution of N-methylpyrrolidinone as reported by Tyman et al. (1989) was found to be a better solvent than ethoxyethanol for this reaction. For example, yields for compounds 4 and 7 (Table I) more than doubled when N-methylpyrrolidinone, rather than ethoxyethanol was used. Yields for reactions in ethoxyethanol and N-methylpyrrolidinone ranged from 23–85% and 49–87% respectively. Compounds 1–13 (Table I) were isolated by adding water and ethyl ether or ethyl acetate to the cooled reaction mixtures which initiated product precipitation and dissolved any unreacted starting materials.

Pharmacology

Twelve of the thirteen bisquinolines set forth in Table I had a significantly lower resistance index than did CQ, and compared favorably with PQ in this regard. The resistance index was apparently unrelated to in vitro or in vivo activity. Eight bisquinolines were more potent than was either CQ and PQ against both clones of P. falciparum. Except for compounds 8 and 12, there was a reasonable correlation between in vitro and in vivo antimalarial activities. For example, compounds 2, 3, 6, 7, and 9–11 which had $IC_{50}$'s less than 6 nM against P. falciparum were either active or curative against P. berghei in vivo. Conversely, compounds 1, 4, 5, and 13 which were approximately an order of magnitude less potent in vitro, were also without activity in vivo. Compound 3, the most potent bisquinoline in vitro, was clearly unique in its in vivo activity; 4/5 and 5/5 mice were cured at 160 and 320 mg/kg, respectively. No other compound was curative at the 160 mg/kg dose.

Methyl substitution in the bridge improved activity, eg. 2 vs. 1 and 7 vs. 6. In the three derivatives (1–3) with a two-carbon bridge, decreased conformational mobility seemed to increase activity. Compounds 4, 5, and 13 with bridges of three, four or twelve carbon atoms were inactive in both screens. However, compounds 6–11 with bridges of between 5 and 9 carbon atoms were active. Molecular modeling using MMX suggests that 4 and 5, unlike 6–11, are not able to achieve a conformation similar to that observed for 3 which suggests that the relative orientation of the two quinoline heterocycles is important for activity.

In summary, the data set forth in Table I is consistent with the excellent results observed in China with PQ against CQ-resistant falciparum malaria. PQ had a resistance index of 1.9 compared to that of 11.2 for CQ. From this data, it is also observed that, like PQ, bisquinolines 1–13 have much lower resistance *indices* than does CQ against CQ-resistant P. falciparum in vitro. Furthermore, six of the thirteen bisquinolines show superior antimalarial activity (both in vitro and in vivo) to CQ. Thus, it is believed that these results support the premise that the bisquinolines of this invention are useful agents against malaria and CQ-resistant malaria, in particular.

EXPERIMENTAL

Melting points were taken with a Mel-Temp capillary apparatus. IR spectra were run as KBr discs on a Perkin Elmer 1420 spectrophotometer. NMR spectra were obtained with either Varian XL-300 or Bruker AC-200 spectrometers using deuteriated dimethyl sulfoxide with TMS as an internal standard. It was not possible to obtain $^{13}$C NMR spectra for 1,4, and 5 due to their low solubilities in DMSO. Microanalyses were performed by M-H-W Laboratories, Phoenix, AZ. The purity of 1–13 was confirmed with silica gel or alumina TLC. 4,7-Dichloroquinoline and the required diamines are commercially available from Aldrich Chemical Co., with the exception of 2-methylpentamethylenediamine and 1,12-dodecanediamine which are available from the Du Pont Company, Petrochemicals Department, Wilmington, Del. All reactions were conducted under a positive pressure of $N_2$ subsequent to ten purge-cycles using a Firestone valve.

Chemistry. Synthesis of Table I Compounds 1–13. A solution of 4,7-dichloroquinoline (10 mmol, 1.98g), triethylamine (10 mmol, 1.01g) and diamine (5 mmol) in either ethoxyethanol or N-methylpyrrolidinone (10 mL) was heated to reflux for 6 to 24 hours under a slight positive N2 pressure. After the reaction mixture cooled to room temperature, ether or ethyl acetate (15 mL) and water (15 mL) were added with stirring and the resulting solid was filtered and washed with water and ethyl acetate or ether to provide 1–13. When required, crystallization of 1–13 was best accomplished from aqueous EtOH.

$N^1N^2$,-Bis(7-chloroquinolin-4-yl)ethane-1, 2-diamine (1): ( 1.63g, 85%); mp 342°–345° C. dec. (lit. mp 334.5°–337° C. (Pearson, et al., 1946)); IR 3460, 3230, 3065, 3020, 2970, 2890, 1610, 1580, 1535 cm–1; $^1$H NMR δ3.62 (m, 4H), 6.58 (d, J=5.4 Hz, 2H), 7.47 (dd, J =9.0 Hz, J=2.4 Hz, 2H), 7.48 (t, J=4.2 Hz, 2H), 7.79 (d, J =2.4 Hz, 2H), 8.23 (d, J=9.0 Hz, 2H), 8.41 (d, J=5.4 Hz, 2H). Anal. ($C_{20}H_{16}Cl_2N_4 \cdot 0.5\ H_2O$) C, H, N.

$N_1,N_2$-Bis(7-chloroquinolin-4-yl)propane1,2-diamine (2): (1.43 g, 72%); mp 287°–289° C. dec.; IR 3440, 3070, 2980, 2930, 1610, 1575, 1535 cm–1 $^1$H NMR δ6 1.35 (d, J=6.3 Hz, 3H), 3.49–3.59 (m, 2H), 4.11–4.20 (m, 1H), 6.55 (d, J=5.7 Hz, 1H), 6.61 (d, J=5.7 Hz, 1H), 7.05 (d, J=8.1 Hz, 1H), 7.44 (dd, J=9.0 Hz, J=2.4 Hz, 1H), 7.46 (t, J=2.4 Hz, 1H), 7.47 (dd, J=9.0 Hz, J=2.4 Hz, 1H), 7.778 (d, J=1.8 Hz, 1H), 7.784 (d, J=1.8 Hz, 1H), 8.22 (d, J=9.0 Hz, 1H), 8.34 (d, J=9.0 Hz, 1H), 8.35 (d, J=5.7 Hz, 1H), 8.40 (d, J=5.7 Hz,1H); $^{13}$C NMR δ17.88, 46.86 46.99, 98.76, 98.93, 117.39, 117.47, 123.86, 124.03, 124.21, 127.43, 127.47, 133.34, 149.05, 149.17, 149.43, 150.10, 151.79, 151.83. Anal. ($C_{21}H_{18}Cl_2N_4$) C, H, N.

±-trans-$N^1,N^2$-Bis ( 7-chloroquinolin-4-Yl) cyclohexane-1,2-diamine (3): (1.55 g, 71%); mp 322°–324° C. dec.; IR 3435, 3250, 3060, 2935, 2860, 1610, 1570, 1535 cm–1; $^1$H NMR δ1.34–1.70 (m, 4H), 1.72–1.91 (m, 2H), 2.02–2.21 (m, 2H), 3.78–3.97 (m, 2H), 6.74 (d, J=5.6 Hz, 2H), 6.94–6.98 (m, 2H), 7.31 (dd, J=8.9 Hz, J=2.0 Hz, 2H), 7.63 (d, J=2.0 Hz, 2H), 8.11 (d, J=9.1 Hz, 2H), 8.28 (d, J=5.5 Hz, 2H) ; $^{13}$C NMR δ24.63, 31.55, 55.50, 99.02, 117.30, 123.54, 124.02, 127.25, 133.09, 149.07, 149.78, 151.55. Anal. ($C_{24}H_{22}Cl_2N_4$) C, H, N.

$N^1,N^3$-Bis(7-chloroquinolin-4-yl)propane1,3-diamine (4): (0.73 g, 37%); mp 312°–314° C. dec.; IR 3450, 3240, 3070, 2960, 2880, 1610, 1580, 1535 cm–1; $^1$H NMR δ2.07 (m, 2H), 3.43 (m, 4H), 6.51 (d, J=5.4 Hz, 2H), 7.40 (t, J=5.3 Hz, 2H), 7.45 (dd, J=9.0 Hz, J =2.4 Hz, 2H), 7.78 (d, J=2.4 Hz, 2H), 8.29 (d, J=9.0 Hz, 2H), 8.37 (d, J=5.4 Hz, 2H). Anal. ($C_{21}H_{18}Cl_2N_4$) C, H, N.

$N_1,N_4$-Bis(7-chloroquinolin-4-yl)butane-1, 4-diamine (5): (1.11 g, 54%); mp 339°–341° C. dec.; IR 3215, 3065, 2960, 1610, 1580, 1550 cm–1 $^1$H NMR δ. Anal. ($C_{22}H_{20}Cl_2N_4$) C, H, N.

$N^1$, $N^5$-Bis(7-chloroquinolin-4-yl)pentane-1,5-diamine (6): (1.07 g, 50%); mp 272°–274° C.; IR 3450, 3250, 3070, 2950, 2880, 1610, 1585, 1535 cm–1 $^1$H NMR δ1.49–1.56 (m, 2H), 1.69–1.78 (m, 4H), 3.25–3.32 (m, 4H), 6.46 (d, J=5.4 Hz, 2H), 7.32 (t, J=5.4 Hz, 2H), 7.44 (dd, J=9.0 Hz, J=2.4 Hz, 2H), 7.78 (d, J=2.4 Hz, 2H), 8.28 (d, J=9.0 Hz, 2H), 8.38 (d, J=5.4 Hz, 2H); $^{13}$C NMR δ24.25, 27.55, 42.33, 98.56, 117.42, 123.88, 124.04, 127.45, 133.28, 149.08, 150.03, 151.85. Anal. ($C_{23}H_{22}Cl_2N_4$) C, H, N.

$N^1$, $N^5$-Bis(7-chloroquinolin-4-yl )-2-methylpentane-1,5-diamine(7 ): (0.50 g, 23%); mp 228°–230° C.; IR 3450, 3065, 2960, 1610, 1580, 1535 cm–1; $^1$H NMR δ0.97 (d, J=6.6 Hz, 3H), 1.23–1.36 (m, 1H), 1.55–2.02 (m, 4H), 3.03–3.51 (m, 4H), 6.44 (d, J=5.4 Hz, 1H), 6.45 (d, J=5.4 Hz, 1H), 7.29 (t, J=5.1 Hz, 1H), 7.36 (d, J=5.7 Hz, 1H), 7.42 (dd, J=9.0 Hz, J=2.1 Hz, 2H), 7.77 (d, J=2.4 Hz, 2H), 8.25 (d, J=9.0 Hz, 1H), 8.29 (d, J=9.0 Hz, 1H), 8.357 (d, J=5.4 Hz, 1H), 8.364 (d, J=5.4 Hz, 1H); $^{13}$C NMR δ7.71, 25.18, 31.26, 31.57, 42.64, 48.66, 98.50, 98.58, 117.39, 123.82, 123.90, 123.97, 127.41, 133.26, 149.04, 149.08, 149.99, 50.14, 151.75, 151.79. Anal. ($C_{24}H_{24}Cl_2N_4$) C, H, N.

$N^1$, $N^6$-Bis(7-chloroquinolin-4-yl)hexane-1,6-diamine (8): (1.55 g, 71%); mp 284°–286° dec.; IR 3450, 3300, 3105, 3065, 3010, 2930, 2830, 1610, 1570, 1535 cm–1; $^1$H NMR δ1.42–1.53 (m, 4H), 1.63–1.74 (m, 4H), 3.23–3.29 (m, 4H), 6.45 (d, J=5.4 Hz, 2H), 7.31 (t, J=5.1 Hz, 2H), 7.43 (dd, J=9.0 Hz, J=2.1 Hz, 2H), 7.77 (d, J=2.1 Hz, 2H), 8.27 (d, J=9.0 Hz, 2H), 8.37 (d, J=5.4 Hz, 2H); $^{13}$C NMR δ 26.37, 27.71, 42.29, 98.52, 117.39, 123.86, 124.02, 127.41, 133.25, 149.06, 150.01, 151.83 Anal. ($C_{24}H_{24}Cl_2N_4$) C, H, N.

$N^1$, $N^7$-Bis(7-chloroquinolin-4-Yl)heptane-1,7-diamine (9): (1.96 g, 87% ); mp 218°–220° C.; IR 3450, 3060, 2935, 2860, 1610, 1580, 1535 cm–1; $^1$H NMR δ1.39 (br s, 6H),1.53–1.77 (m, 4H), 3.16–3.32 (m, 4H), 6.44 (d, J=5.5 Hz, 2H), 7.31 (t, J=5.1 Hz, 2H), 7.44 (dd, J=9.0 Hz, J=2.2 Hz, 2H), 7.79 (d, J=2.2 Hz, 2H), 8.29 (d, J=9.1 Hz, 2H), 8.39 (d, J=5.4 Hz, 2H) ; $^{13}$C NMR δ26.64, 27.73, 28.64, 42.35, 98.54, 117.43, 123.91, 124.08, 127.46, 3.30, 149.09, 150.04, 151.87Anal. ($C_{25}H_{26}Cl_2N_4$) C, H, N.

$N^1$, $N^8$-Bis(7-chloroquinolin-4-yl)octane-1,8diamine (10): (1.80 g, 77%); mp 216°–219° C.; IR 3450, 3350, 3070, 2940, 2865, 1610, 1580, 1540 cm–1; $^1$H NMR δ1.35 (br s, 8H),1.57–1.75 (m, 4H), 3.15–3.31 (m, 4H), 6.44 (d, J =5.5 Hz, 2H), 7.28 (t, J =5.1 Hz, 2H), 7.43 (dd, J=9.0 Hz, J=2.3 Hz, 2H), 7.77 (d, J=2.2 Hz, 2H), 8.27 (d, J=9.1 Hz, 2H), 8.38 (d, J=5.4 Hz, 2H); $^{13}$C NMR δ26.58, 27.73, 28.79, 42.36, 98.55, 117.42, 123.92, 124.08, 127.44, 33.30, 149.08, 150.04, 151.87. Anal. ($C_{26\ 28}Cl_2N_4$) C, H, N.

$N^1$, $N^9$-Bis(7-chloroquinolin-4-yl)nonane-1,9-diamine (11): (82g, 76%); mp 161°–164° C.; IR 3455, 3370, 3065, 2930, 2860, 1610, 1575, 1540, 1535 cm–; $^1$H NMR δ1.14–1.50 (br s, 10H),1.54–1.73 (m, 4H), 3.13–3.32 (m, 4H), 6.44 (d, J=5.5 Hz, 2H), 7.28 (t, J=5.1 Hz, 2H), 7.43 (dd, J=9.0 Hz, J=2.3 Hz, 2H), 7.77 (d, J=2.2 Hz, 2H), 8.28 (d, J=9.0 Hz, 2H), 8.38 (d, J=5.4 Hz, 2H) ; $^{13}$C NMR δ26.61, 27.74, 28.78, 28.98, 42.37, 98.53, 117.43, 123.90, 124.08, 127.46, 133.30, 149.09, 150.04, 151.87. Anal. ($C_{27}H_{30}Cl_2N_4$) C, H, N.

$N^1$, $N^{10}$-Bis(7-chloroquinolin-4-yl)decane-1,10-diamine (12): (2.15g, 87%); mp 200°–204° C.; IR 3445, 3285, 3060, 2930, 2855, 1610, 1580, 1535 cm–; $^1$H NMR δ1.28 (br s, 12H), 1.52–1.74 (m, 4H), 3.15–3.31 (m, 4H), 6.44 (d, J=5.4 Hz, 2H), 7.28 (t, J=5.1 Hz, 2H), 7.43 (dd, J=8.9 Hz, J=2.3 Hz, 2H), 7.70 (d, J=2.2 Hz, 2H), 8.27 (d, J=7.0 Hz, 2H), 8.38 (d, J=5.4 Hz, 2H) ; $^{13}$C NMR δ26.70, 27.72, 28.80, 28.94, 42.37, 98.53, 117.44, 123.89, 124.08, 127.46, 133.29, 149.10, 150.04, 151.86. Anal. ($C_{38}H_{32}Cl_2N_4$) C, H, N.

$N^1N^{12}$-Bis(7-chloroquinolin-4-yl)dodecane-1,12-diamine (13 ): (1.70g, 65%); mp 188°–190° C.; IR 3460, 3070, 2930, 2860, 1610, 1580, 1540 cm–1 $^1$H NMR δ1.24–1.35 (m, 16H),1.59–1.69 (m, 4H), 3.22–3.28 (m, 4H), 6.46 (d, J=5.7 Hz, 2H), 7.57 (t, J=5.3 Hz, 2H), 7.44 (dd, J=9.0 Hz, J=2.1 Hz, 2H), 7.78 (d, J=2.1 Hz, 2H), 8.29 (d, J=9.0 Hz, 2H), 8.39 (d, J=5.7 Hz, 2H); $^{13}$C NMR δ18.49, 25.42, 26.55, 27.69, 28.74, 28.91, 42.34, 55.97 98.52, 117.41, 123.86, 124.05, 127.41, 133.26, 149.07, 150.03, 151.83. Anal. ($C_{30}H_{36}Cl_2N_4 \cdot$ HO) C, H, N.

Analytical Data (1) Anal. Calcd. for $C_{20}H_{16}Cl_2N_4 \cdot 0.5\ H_2O$: C, 61.23; N, 4.37; N, 14.28. Found: C, 61,36; H, 4,46; N, 14.26.

(2) Anal. Calcd. for $C_{21}H_{18}Cl_2N_4$: C, 63.48; H, 4.57; N, 14.10. Found: C, 63.49; H, 4.71; N, 4.18.

(3) Anal. Calcd. for $C_{24}H_{22}Cl_2N_4$: C, 65.91; H, 5.07; N, 12.81. Found: C, 65.71; H, 5.16; N, 12.69.
(4) Anal. Calcd. for $C_{21}H_{18}Cl_2N_4$: C, 63.48; H, 4.57; N, 14.10. Found: C, 63.25; H, 4.65; N, 14.15.
(5) Anal. Calcd. for $C_{22}H_{20}Cl_2N_4$: C, 64.24; H, 4.90; N, 13.62. Found: C, 64.07; H, 4.83; N, 13.56.
(6) Anal. Calcd. for $C_{23}H_{22}Cl_2N_4$: C, 64.94; H, 5.21; N, 13.17. Found: C, 65.15; H, 5.21; N, 13,31.
(7) Anal. Calcd. for $C_{24}H_{24}Cl_2N_4$: C, 65.61; H, 5.51 ; N, 12.75. Found: C, 65.43; H, 5.58; N, 12.59.
(8) Anal. Calcd. for $C_{24}H_{24}Cl_2N_4$: C, 65.61; H, 5.51; N, 12.75. Found: C, 65.38; H, 5.69; N, 12.71.
(9) Anal. Calcd. for $C_{25}H_{26}Cl_2N_4$: C, 66.22; H, 5.78; N, 12.36. Found: C, 66.35; H, 5.82; N, 12.33.
(10) Anal. Calcd. for $C_{26}H_{28}Cl_2N_4$; C, 66.81; H, 6.04; N, 11.99. Found: C, 66.96; H, 6.28; N, 11.99.
(11) Anal. Calcd. for $C_{27}H_{30}Cl_2N_4$: C, 67.35; H, 6.28; N, 11.64. Found: C, 67.43; H, 6.36; N, 11.75.
(12) Anal. Calcd. for $C_{28}H_{32}Cl_2N_4$: C, 67.87; H, 6.51; N, 11.31. Found: C, 68.02; H, 6.63; N, 11.35.
(13) Anal. Calcd, for $C_{30}H_{36}Cl_2N_4$, $H_2O$: C, 66.53; H, 7.07; N, 10.35. Found: C, 66.80; H, 7.32; N, 9.93.

Pharmacological Methods

In vitro activity against *P. falciparum* was determined using a modification of the semiautomated microdilution technique of Desjardins et al. (1979) and Milhous et al. (1985). Two *P. falciparum* malaria parasite clones, designated as Sierra Leone (D-6) and Indochina (W-2), are used in susceptibility testing. The former is resistant to mefloquine, and the latter to CQ, pyrimethamine, sulfadoxine, and quinine. Test compounds are dissolved in dimethylsulfoxide, and solutions serially diluted with culture media. Erythrocytes with 0.25 to 0.5% parasitemia are added to each well of a 96-well microdilution plate to give a final hematocrit of 1.5%. Inhibition of uptake of tritiated hypoxanthine is used as an index of antimalarial activity. Results are reported as $IC_0$ (ng/mL) values. For a complete description of this assay, see Milhous et al. (1985) and Lin et al. (1987).

In vivo activity against *P. berghei* was obtained against a drug-sensitive strain of *P. berghei* (strain KBG 173) (Osdene et al., 1967). Each test compound is administered subcutaneous to five male mice per dilution in a single subcutaneous dose 3 days after infection. Results are expressed in T-C values which indicate the mean survival time of the treated mice beyond that of the control animals; untreated mice survive on average 6.2 days. Compounds are classified as active (A) when the mean survival time of the treated mice is twice that of the controls (>6.2 days), and curative (C) when one or more test animals live 60 days post-infection. Deaths from 0–2 days post-treatment are attributed to toxicity (T).

The compounds set forth in the following Table I have the formula:

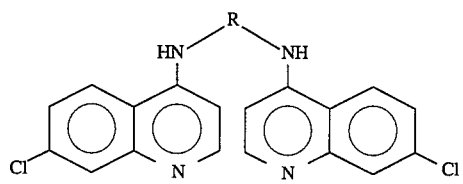

wherein R is as defined in the Table.

TABLE I

Antimalarial Activity of 1–13 against *P. falciparum* in vitro and *P. berghei* in vivo

| Compound | R | P. falciparum $IC_{50}$ (nM) | | Resistance Index[a] | P. berghei T-C (days)[b] | | |
|---|---|---|---|---|---|---|---|
| | | D-6 | W-2 | | 40 | 160 | 640 mg/kg |
| 1 | $(CH_2)_2$ | 17.3 | 27.0 | 1.6 | 0.0 | 0.4 | 1.4 |
| 2 | $CH_2CH(CH_3)$ | 3.5 | 3.9 | 1.1 | 3.4 | 5.7 | C-3 |
| 3 | trans-1,2-cyclohexyl | 1.0 | 1.4 | 1.4 | 8.5 | C-4 | NA[c] |
| 4 | $(CH_2)_3$ | 15.1 | 82.9 | 5.5 | 0.2 | 0.4 | 1.2 |
| 5 | $(CH_2)_4$ | 387 | 80.9 | 0.2 | 0.5 | 2.3 | 5.6 |
| 6 | $(CH_2)_5$ | 2.5 | 3.8 | 1.5 | 1.0 | 5.1[d] | C-1[d] |
| 7 | $(CH_2)_3CH(CH_3)CH_2$ | 2.7 | 3.0 | 1.1 | 1.2 | 3.6 | C-2[d] |
| 8 | $(CH_2)_6$ | 21.1 | 23.4 | 1.1 | 0.4 | 3.9 | C-1 |
| 9 | $(CH_2)_7$ | 1.9 | 4.3 | 2.3 | 2.6 | 7.2[d] | C-3[d] |
| 10 | $(CH_2)_8$ | 5.6 | 3.1 | 0.6 | −0.2 | 1.0 | C-1 |
| 11 | $(CH_2)_9$ | 3.0 | 2.3 | 0.8 | 3.1 | 7.4[d] | 15.0A[d] |
| 12 | $(CH_2)_{10}$ | 5.7 | 3.4 | 0.6 | 0.2 | 0.2 | 0.6 |
| 13 | $(CH_2)_{12}$ | 59.7 | 30.8 | 0.5 | 0.0 | −0.2 | 0.0 |
| CQ | — | 8.9 | 99.6 | 11.2 | 8.7 | C-1 | C-1,T-3[e] |
| PQ | — | 8.3 | 16.1 | 1.9 | — | — | — |

[a]$IC_{50}$(W-2)/$IC_{50}$(D-6) ratio.
[b]T-C is the mean survival time of the treated mice beyond that of the control animals (single does administered s.c. 3 days post infection, n = 5). This value must be ≥ twice the mean survival time (6.2 days) of the control animals to be considered active (A). Survival beyond 60 days is considered curative (C), and deaths from 0–2 days post-treatment are attributed to toxicity (T).
[c]C-5 at 320 mg/kg.
[d]Skin lesions observed at site of injection.
[e]T-C values for CQ represent averages of ten best data sets from WRAIR.

Therapeutic doses and formulations

The compounds of this invention can be administered to the host or patient as an active ingredient in a variety of dosage forms. In addition to the active ingredient, which may be in the form of a pharmaceutically-acceptable derivative, such as a pharmaceutically-acceptable salt, any of a number of pharmaceutically-acceptable excipients which facilitate processing of the active compound into suitable pharmaceutical preparations can be used to formulate these compositions. These are well known and need not be detailed here (e.g., see *Remington's, Pharmaceutical Sci-* ences, 1985). Because the bisquinolines of this invention are active orally, dosage forms designed for oral administration are preferred. Exemplary are tablets, capsules, and dragees. In some cases, for example, where the host is seriously ill and time is of the essence, it may be necessary to administer the compounds of this invention parenterally. In such cases intravenous administration is usually preferred. However, other dosage forms designed for parenteral administration can also be employed, e.g., subcutaneous or rectal (usually suppositories).

Appropriate formulations for parenteral administration include aqueous solutions of the active compound prepared in a water-soluble or water-dispersible form. Alternatively, the active compounds may be administered as suspensions in appropriate oily injection carriers, i.e., in suitable lipophilic carriers, such as fatty oils (sesame oil being an example), or synthetic fatty acid esters (ethyl oleate or triglycerides being examples). Pharmaceutical formulations prepared for aqueous injection may contain substances which increase the viscosity or the suspension such as, for example, sodium carboxymethyl cellulose, sorbitol, and/or dextran.

The therapeutic bisquinolines of the present invention may also be administered encapsulated in liposomes. In such pharmaceutical preparations, the active compound is contained in corpuscles which consist of concentric aqueous layers interspersed between hydrophobic lipidic layers. The bisquinolines, depending upon their solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such as a diacetylphosphate, stearylamine, or phosphatidic acid, and/ or other materials of a hydrophobic nature which are generally well known in the art.

To be available for use in systemic administration, the therapeutic bisquinolines must be formulated into suitable pharmaceutical compositions; the protocol for systemic administration would use a therapeutic approach compatible with the particular formulation selected. Pharmaceutical compositions within the scope of the present invention include those compositions where the bisquinoline is contained in an effective amount sufficient to kill the malaria-inducing parasite without causing unacceptable toxicity for the host or patient. The therapeutic amount which represents an effective anti-malaria dose sufficient for treatment of each of the various types of malaria remains to be determined empirically by those skilled in the art of designing and administering anti-malarials. However, it has been determined that the bisquinolines of this invention appear to have high therapeutic indices, thus presenting a wide range of effective dosage options and strategies. A preferred dosage range is from about 5 to about 100 milligrams of bisquinoline per milligram of host body weight, given three times a day. Doses as high as 500 mg/kg, or even higher, thrice daily can be given, but are not economically practical in the usual case of malaria encountered. As a practical matter, any dose which is sufficient to achieve an effective blood concentration of from about 0.05 to about 0.2 µg/mL can be employed.

References

Benazet, F. *Plasmodium berghei* et antimalariques a action de longue duree. *Ann. Soc. Belge. Med. Trop.* 1965, 45, 459–466.

Benazet, F. Activite D'un Nouvel Antimalarique, Le 16.126 R. P. Sur Le Paludisme Experimental Des Animaux De Laboratoire. *Bull. Soc. Pathol. Exot.* 1967, 60, 221–228.

Chen. L., Qu, F.-Y.; Zhou, Y.-C. Field Observations on the Antimalarial Piperaquine. *Chin. Med. J.* 1982, 95, 281–286.

Cowman, A. F.; Foote, S. J. Chemotherapy and Drug Resistance in Malaria. *Int. J. Parasitol.* 1990, 20, 503–513.

Desjardins, R. E., Canfield, C. J., Haynes, J. D., and Chulay, J. D. Quantitative assessment of antimalarial activity in vitro by a semiautomated microdilution technique. *Antimicrob. Agents Chemother.* 1979, 16, 710–718.

Geary, T. G.; Divo, A. A.; Jensen, J. B. Activity of quinoline-containing antimalarials against chloroquine-sensitive and -resistant strains of *Plasmodium falciparum* in vitro. *Trans. R. Soc. Trop. Med. Hyg.* 1987, 81, 499–503.

Geary, T. G.; Jensen, J. B. Lack of Cross-Resistance to 4-Aminoquinolines in Chloroquine-Resistant *Plasmodium Falciparum* In Vitro. *J. Parasitol.* 1983, 69, 97–105.

Knowles, G.; Davidson, W. L.; Jolley, D.; Alpes, M.P. The relationship between the in vitro response of *Plasmodium falciparum* to chloroquine, quinine and mefloquine. *Trans. Roy. Soc. Trop. Med. Hyg.* 1984, 78, 146–150.

LeBras, J., Deloron, P., and Charmot, G. Dichloroquinazine (A 4-Aminoquinoline) Effective In Vitro Against Chloroquine-Resistant *Plasmodium Falciparum*. *Lancet* 1983, 1, 73–74.

Lafaix, C.; Rey, M.; Diop Mar, I.; Nouhouayi, A. Essai de traitement curatif du paludisme pour un nouvel antipaludique de synthese, le 16,126 RP. *Bull. Soc. Med. Afr. Noire Langue Fr.* 1967, 12, 546–551.

Li, Y.; Hu, Y.; Huang, H.; Zhu, D.; Huang, W.; Wu, D.; Qian, Y. Hydroxypiperaquine Phosphate in Treatment of Falciparum Malaria. *Chin. Med. J.* 1981a, 94, 301–302.

Li, Y.; Qin, Y.; Qu, Y.; Gong, J. Hydroxypiperaquine Phosphate in Treating Chloroquine Resistant Falciparum Malaria. *Chin. Med. J.* 1981b, 94, 303–304.

Li, Y.; Chen, L.; Dai. Z.-R.; Gong, J.-Z. Antimalarial Activities of Hydroxypiperaquine and its Phosphate against *Plasmodium Berghei* and *P. cynomolgi*. *Acta Pharmacol. Sinica* 1984, 5, 57–60.

Li, J.; Huang, W.-J. Effects of artesunate, pyronaridine and hydroxypiperaquine on chloroquine-sensitive and chloroquine-resistant isolates of *Plasmodium falciparum* in vitro. *Acta Pharmacol. Sinica* 1988, 9, 83–86.

Lin, A. J.; Klayman, D. L.; Milhous, W. K. Antimalarial Activity of New Water-Soluble Dihydroartemisinin Derivatives. *J. Med. Chem.* 987, 30, 2147–2150.

Lin, C.; Qu, F.-Y.; Zhou, Y.-C. Field Observations on the Antimalarial Piperaquine. Chin. Med. J. 1982, 95, 281–286.

Milhous, W. K.; Weatherly, N. F.; Bowdre, J. H.; Desjardins, R. E. In vitro activities of and mechanisms of resistance to antifol antimalarial drugs. *Antimicrob. Agents Chemother.* 1985, 27, 525–530.

Oduola, A.M. J.; Weatherly, N. F.; Bowdre, J. H.; Desjardins, R. E. *Plasmodium falciparum*: Cloning by Single-Erythrocyte Micromanipulation and Heterogeneity in Vitro. *Exp. Parasitol.* 1988, 66, 86–95.

Osdene, T. S.; Russell, P. B.; Rane, L. 2,3,7-Triamino-6-substituted arylpteridines. A new series of potent antimalarial agents. *J. Med. Chem.* 1967, 10, 431–434.

Payne, D. Spread of Chloroquine Resistance in *Plasmodium falciparum*. *Parasitol. Today* 1987, 3, 241–246.

Pearson, D. E.; Jones, W. H.; Cope, A. C. Synthesis of Monoalkyl-substituted Diamines and their Condensation Products with 4,7-Dichloroquinoline. *J. Amer. Chem. Soc.* 1946, 68, 1225–1229.

*Remington's Pharmaceutical Sciences*, 17th Ed., 1985, A. R Gennaro, Ed., Mack Publishing Co., Easton, Pa.

Schmidt, L. H.; Vaughan, D.; Mueller, D.; Crosby, R.; Hamilton, R. Activities of Various 4-Aminoquinolines Against Infections with Chloroquine-Resistant Strains of *Plasmodium falciparum. Antimicrob. Agents Chemother.* 1977, 11, 826–843.

Singh, T.; Hoops, J. F.; Biel, J. H.; Hoya, W. K.; Stein, R. G.; Cruz, D. R. Antimalarials. "Distal" Hydrazine Derivatives of 7-Chloroquinoline. *J. Med. Chem.* 1971, 14, 532–535.

Sowunmi, A.; Salako, L. A.; Walker, O.; Ogundahunsi, O. A. T. Clinical efficacy of mefloquine in children suffering from chloroquine-resistant *Plasmodium falciparum* malaria in Nigeria. *Trans. R. Soc. Trop. Med. Hyg.* 1990, 84, 761–764.

Sturchler, D. How much Malaria is there Worldwide? *Parasitol. Today* 1989, 5, 39–40.

Tyman, J.; Ghorbanian, S.; Muir, M.; Tychopoulous, V.; Bruce, I.; Fisher, I. Improved Nucleophilic Displacements in N-Methylpyrrolidinone as a Solvent. *Synthetic Comm.* 1989, 19, 179–188.

Warhurst, D.C. Chloroquine-Resistant Rodent Malaria and the Long-Acting Antimalarial 12,278 R. P. *Trans, R. Soc. Trop. Med. Hyg.* 1966, 60, 565–566.

Watkins, W. M.; Sixsmith, D. G.; Spencer, H. C.; Boriga, D. A.; Kariuki, D. M.; Kipingor, T.; Koech, D. K. Effectiveness of Amodiaquine as Treatment for Chloroquine-Resistant *Plasmodium Falciparum* Infections in Kenya. *Lancet* 1984, 357–359.

Zhang, K.; Zhou, J.; Wu, Z.; Huang, Q. Susceptibility of *Plasmodium falciparum* to Chloroquine, Piperaquine, Amodiaquine, Mefloquine and Quinine with In Vitro Microtechnique in Hainan Island. *Chin. J. Parasitol. Parasitic Dis.* 1987, 5, 165–169.

What is claimed is:

1. A compound having the following formula:

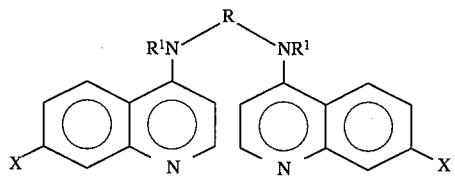

wherein R is a bivalent radical derived from an acyclic or cyclic hydrocarbon by removal of one hydrogen atom from each of two different carbon atoms; R' is hydrogen or lower alkyl, and wherein X is hydrogen (—H), halo, trifluoromethyl (—CF$_3$), cyano (—CN), or methylsulfoxide (—SOCH$_3$); and wherein, in its acyclic form, R contains at least three and no more than 12 carbon atoms, and in its cyclic form, R contains at least three and no more than eight carbon atoms.

2. A compound of the following formula:

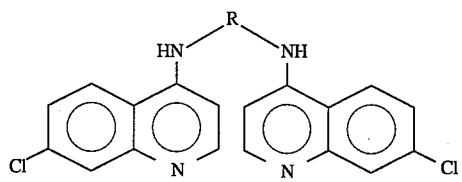

wherein R is selected from the group consisting of CH$_2$CH(CH$_3$), (CH$_2$)$_3$, (CH$_2$)$_4$, (CH$_2$)$_5$, (CH$_2$)$_3$CH(CH$_3$)CH$_2$, (CH$_2$)$_6$, (CH$_2$)$_7$, (CH$_2$)$_8$, (CH$_2$)$_9$, (CH$_2$)$_{10}$, (CH$_2$)$_{11}$, and (CH$_2$)$_{12}$, and between C1 and C4 lower alkyl substituted derivatives thereof.

3. A compound of the following formula:

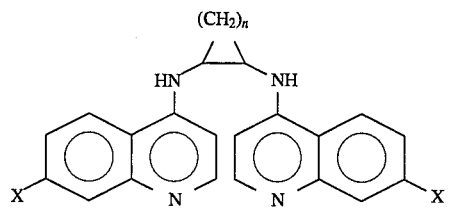

wherein X is hydrogen (—H), fluoro (—F), chloro (—Cl), bromo (—Br), trifluoromethyl (—CF$_3$), cyano (—CN), or methylsulfoxide (—SOCH$_3$) and n is a whole integer from 1 through 6.

4. The compound of claim 3 wherein n is 4 and X is chloro.

5. The compound of claim 2 wherein R is CH$_2$CH(CH$_3$).

6. The compound of claim 2 wherein R is (CH$_2$)$_3$.

7. The compound of claim 2 wherein R is (CH$_2$)$_4$.

8. The compound of claim 2 wherein R is (CH$_2$)$_5$.

9. The compound of claim 2 wherein R is (CH$_2$)$_3$CH(CH$_3$)CH$_2$.

10. The compound of claim 2 wherein R is (CH$_2$)$_6$.

11. The compound of claim 2 wherein R is (CH$_2$)$_7$.

12. The compound of claim 2 wherein R is (CH$_2$)$_8$.

13. The compound of claim 2 wherein R is (CH$_2$)$_9$.

14. The compound of claim 2 wherein R is (CH$_2$)$_{10}$.

15. The compound of claim 2 wherein R is (CH$_2$)$_{11}$.

16. The compound of claim 2 wherein R is (CH$_2$)$_{12}$.

17. An anti-malaria composition containing an effective amount of ±-Trans-N$^1$, N$^2$-Bis(7-chloroquinolin-4-yl)-cyclohexane-1,2-diamine in a pharmaceutically acceptable carrier.

18. A method for the treatment of malaria comprising administering to a host an N,N-bis(7-substituted-quinolin-4-yl)alkane diamine of claims 1–17 in a pharmaceutically acceptable carrier containing an amount of said diamine which is effective in treating malaria.

19. The method of claim 18 wherein the effective dose for treating malaria is that dose which is toxic to the malaria parasite infecting the host, but below the threshold of significant toxicity to the host.

20. An antimalarial composition comprising the compounds of claims 1–17 in a pharmaceutically acceptable carrier.

* * * * *